United States Patent [19]

Fachinetti et al.

[11] 4,039,566
[45] Aug. 2, 1977

[54] PROCESS FOR THE PREPARATION OF TITANIUM THIO-DERIVATIVES

[75] Inventors: Giuseppe Fachinetti, Fauglia; Carlo Floriani, Pisa, both of Italy

[73] Assignee: Snam Progetti S.p.A., Milan, Italy

[21] Appl. No.: 572,649

[22] Filed: Apr. 29, 1975

[30] Foreign Application Priority Data

May 17, 1974   Italy .................................. 22868/74

[51] Int. Cl.$^2$ ............................................... C07F 7/28
[52] U.S. Cl. .......................... 260/429.5; 260/429 CY
[58] Field of Search ....................... 260/429.5, 429 CY

[56] References Cited

U.S. PATENT DOCUMENTS

| | | | |
|---|---|---|---|
| 3,030,395 | 4/1962 | Giddings | 260/429.5 |
| 3,361,777 | 1/1968 | King | 260/429 |
| 3,644,447 | 2/1972 | Joshi | 260/429 R |

OTHER PUBLICATIONS

Coutts et al., Aus. J. Chem. V19, 1377–1380 (1966).
Advances in Organometallic Chemistry, vol. 9, pp. 175–176, (1970).

*Primary Examiner*—Helen M. S. Sneed
*Attorney, Agent, or Firm*—Ralph M. Watson

[57] ABSTRACT

A thio-derivative of titanium, represented by the formulae:

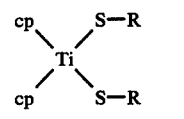

or

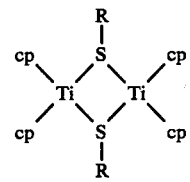

wherein *cp* is a cyclopentadiene and R is an alkyl, aryl or cycloalkyl radical, is prepared by reacting a carbonyl derivative of titanium, represented by the formula: Ti $cp_2(CO)_2$, wherein *cp* has the meaning given above, with a disulfide represented by the formula: $R_2S_2$, wherein R has the meaning given above, in an inert atmosphere.

4 Claims, No Drawings

PROCESS FOR THE PREPARATION OF TITANIUM THIO-DERIVATIVES

The present invention relates to a process for the preparation of thio-derivatives of titanium from its carbonyl derivatives.

More specifically the subject of the present invention is a process for the preparation of titanium thio-derivatives, mono-nuclear or di-nuclear, usable as polymerization catalysts of the formulae, respectively

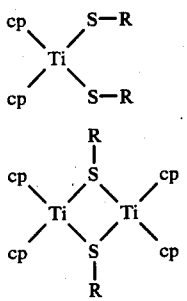

where cp is a cyclopentadiene and R is an alkyl, aryl, or cycloalkyl radical, from the compound Ticp$_2$(CO)$_2$ The reaction for the preparation of the mono-nuclear compound is carried out between said carbonyl derivative and a disulfide of the formula R$_2$S$_2$ and runs according to the following pattern $$\text{Ticp}_2(\text{CO})_2 + R_2S_2 \rightarrow cp_2Ti(SR)_2 + 2CO \quad (1)$$

the reagents being fed in the ratio 1:1.

The mono-nuclear Titanium compound may subsequently be reacted with Ticp$_2$(CO)$_2$ to give the di-nuclear derivative according to the reaction $$cp_2Ti(SR)_2 + \text{Ticp}_2(\text{CO})_2 \rightarrow (\text{Ticp}_2SR)_2 + 2CO$$

or alternatively the di-nuclear product may be obtained in the same reaction vessel by feeding the carbonyl and the disulfide in the ratio 2:1, so that reaction (1) does not stop at the mononuclear compound, but runs until the formation of compound (b).

All the operating procedures will be more evident from an examination of the following examples.

All the operations here referred to were carried out in an inert atmosphere and the solvents used were purified through known methods.

EXAMPLE 1

0.6 g (2.44 mmoles) of pure p-tolyldisulfide were added to a solution of 0.52 g (2.22 mmoles) of Ticp$_2$(CO)$_2$ (1) in 25 cc heptane. A rapid production of CO was observed and the solution changed from brown to purple. After half an hour crystals of Ticp$_2$(SC$_6$H$_4$Me-p)$_2$(V) separated, with a yield of about 62%.

Likewise titanium derivatives may be prepared with formula (a) where R is CH$_3$ (II), Ph (III), Ph CH$_2$ (IV) (Ph = phenyl).

The test results and some product properties are reported in the table.

EXAMPLE 2

A. A solution of 0.87 g (4.15 mmoles) of Ticp$_2$(CO)$_2$ (1) and 0.650 (4.15 mmoles) of Ticp$_2$(SPh)$_2$ (III) in 50 cc toluene was refluxed for 10 minutes. Rapidly CO was produced and at the same time a crystalline purpish solid precipitated.

The solid was collected, washed with toluene and dried (yield 67%) and tested for Ticp$_2$(SPh)$_2$ (VI).

B. A solution consisting of 6.8 g (29 mmoles) of compound (1) and 3 g (13.8 mmoles) of Ph$_2$S$_2$ in 100 cc of toluene was refluxed for about 30 minutes. The solution became purple and, while CO was being developed, a crystalline solid, dark purple, precipitated, which, washed and dried, was tested for (VI) with a yield of about 90%.

Likewise titanium (b) di-nuclear compounds may be prepared, where R is p-Me C$_6$H$_4$ (VII) and C$_2$H$_5$ (VIII).

Test results and some product properties are reported in table.

TABLE

Analytic and magnetic results for titanium thio-derivatives

| | Complex | Analytic data C | % H | (% calc.) S | μ eff./TK B. I.[b] | P. H.[a] |
|---|---|---|---|---|---|---|
| (II) | Ticp$_2$(SME)$_2$ | 53,1 (52,9) | 5,7 (5,9) | 27,8 (27,2) | — | 341 (396) |
| (III) | Ticp$_2$(SPh)$_2$ | 66,4 (66,7) | 5,1 (5,1) | 16,6 (16,2) | — | 430 (424) |
| (IV) | Ticp$_2$(SCH$_2$Ph)$_2$ | 68,0 (67,9) | 5,7 (5,7) | 14,6 (15,1) | — | 369 (424) |
| (VI) | [Ticp$_2$(SPh)]$_2$ | 66,3 (66,9) | 5,2 (5,2) | 10,8 (11,1) | 1,43/291 | |
| (VII) | [Ticp$_2$(SC$_6$H$_4$Me-p)]$_2$ | 67,3 (67,8) | 5,8 (5,7) | 10,3 (10,6) | 1,43/292 | |
| (VIII) | [Ticp$_2$(SEt)]$_2$ | 61,4 (60,3) | 6,9 (6,3) | 13,4 (13,4 | 1,13/295 | |

[a]Determined with cryoscopic measurement in benzene
[b]Results expressed for metal atom
Magnetic measurement effected with Guoy balance

What we claim is:

1. The process of preparing a thio-derivative of titanium represented by the formulae:

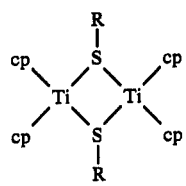

wherein cp represents a cyclopentadiene and R represents an alkyl, aryl or cycloalkyl radical, which comprises reacting a carbonyl derivative of titanium represented by the formula: Ticp$_2$(CO)$_2$, wherein cp has the meaning given above, with a disulfide represented by the formula: $R_2S_2$, wherein R has the meanings given above, in an inert atmosphere.

2. The process of preparing a thio-derivative of titanium represented by the formula:

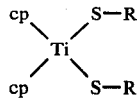

wherein cp represents a cyclopentadiene and R represents an alkyl, aryl or cycloalkyl radical, as claimed in claim 5, wherein the reaction between said carbonyl derivative of titanium and said disulfide is carried out in the ratio of 1:1.

3. The process of preparing a thio-derivative of titanium represented by the formula:

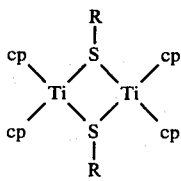

wherein cp represents a cyclopentadiene and R represents an alkyl, aryl or cycloalkyl radical, as claimed in claim 5, wherein the reaction between said carbonyl derivative of titanium and said disulfide is carried out in the ratio of 2:1.

4. The process of preparing a thio-derivative of titanium represented by the formula:

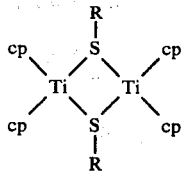

wherein cp represents a cyclopentadiene and R represents an alkyl, aryl or cycloalkyl radical, wherein a carbonyl derivative of titanium represented by the formula: $Ticp_2(CO)_2$, wherein cp has the meaning given above, is reacted with a thio-derivative of titanium prepared as claimed in claim 1, and represented by the formula:

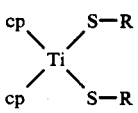

wherein cp and R have the meanings given above.

* * * * *

UNITED STATES PATENT AND TRADEMARK OFFICE
CERTIFICATE OF CORRECTION

PATENT NO. : 4,039,566

DATED : August 2, 1977

INVENTOR(S) : Giuseppe Fachinetti and Carlo Floriani

It is certified that error appears in the above-identified patent and that said Letters Patent are hereby corrected as shown below:

Column 1, line 56, to the right of formula insert --(2)--.

In the table, Under heading "Complex", first line, Correct "(SME)$_2$" to read --(SMe)$_2$--.

Column 3, line 13, Correct "claim 5" to read --claim 1--.

line 29, Correct "claim 5" to read --claim 1--.

Signed and Sealed this

Fourteenth Day of February 1978

[SEAL]

Attest:

RUTH C. MASON
*Attesting Officer*

LUTRELLE F. PARKER
*Acting Commissioner of Patents and Trademarks*